(12) United States Patent
Xu et al.

(10) Patent No.: US 6,714,871 B1
(45) Date of Patent: Mar. 30, 2004

(54) METHOD FOR QUANTIFYING PERMEABILITY OF VUGGY CARBONATES USING WIRELINE LOGS

(75) Inventors: Chunming Xu, Katy, TX (US); Bill M. Newberry, Sugar Land, TX (US)

(73) Assignee: Schlumberger Technology Corporation, Sugar Land, TX (US)

(*) Notice: Subject to any disclaimer, the term of this patent is extended or adjusted under 35 U.S.C. 154(b) by 0 days.

(21) Appl. No.: 10/065,581

(22) Filed: Oct. 31, 2002

(51) Int. Cl.[7] .............................................. G01N 15/08
(52) U.S. Cl. .............................................. 702/12; 702/6
(58) Field of Search ................. 702/12, 6, 13; 324/303

(56) References Cited

U.S. PATENT DOCUMENTS

| | | | |
|---|---|---|---|
| 5,193,059 A | * 3/1993 | Tiab et al. | 702/12 |
| 5,680,043 A | * 10/1997 | Hurlimann et al. | 324/303 |
| 5,809,163 A | 9/1998 | Delhomme et al. | 382/109 |
| 5,828,981 A | * 10/1998 | Callender et al. | 702/6 |
| 5,869,755 A | * 2/1999 | Ramamoorthy et al. | 73/152.05 |
| 6,088,656 A | * 7/2000 | Ramakrishnan et al. | 702/13 |
| 6,484,102 B1 | * 11/2002 | Holmes | 702/6 |

* cited by examiner

Primary Examiner—Marc S. Hoff
Assistant Examiner—Anthony Gutierrez
(74) Attorney, Agent, or Firm—Brigitte L. Jeffery; John Ryberg

(57) ABSTRACT

A method for quantifying permeability of a vuggy reservoir includes determining a permeability modeled with matrix porosity ($K_0$) of the reservoir, determining a vug porosity ($\Phi_{vug}$) of the reservoir, and quantifying permeability (K) of the reservoir as follows:

$$K = aK_0 \cdot b^{c\Phi_{vug}},$$

where a, b, and c are constants.

20 Claims, 3 Drawing Sheets

METHOD FOR QUANTIFYING PERMEABILITY OF VUGGY CARBONATES USING WIRELINE LOGS

BACKGROUND OF INVENTION

The invention relates to evaluation of rock formations. More specifically, the invention relates to a method for quantifying permeability of a vuggy reservoir.

A reservoir is a rock formation in which hydrocarbons have accumulated. Before producing hydrocarbons from the reservoir, it is usually desirable to quantify the properties of the reservoir. Among the most important properties are the porosity and permeability of the reservoir. The term "porosity" refers to the volume of the pore space expressed as a percent of the total volume of the rock mass, or that volume within the rock formation that can contain fluids. The term "permeability" refers to a measurement of the rock formation's ability to transmit fluids. Formations that transmit fluids readily, such as sandstones and carbonates with larger and well-connected pores, are described as permeable. Impermeable rocks, such as shales and siltstones, tend to be finer-grained or of a mixed grain size, with smaller, fewer, or less interconnected pores. The ability to accurately quantify the porosity and permeability of a reservoir volume is essential for production planning and ultimate hydrocarbon recovery, i.e., the percentage of total hydrocarbons producible from the reservoir over its entire lifespan.

Sandstones usually have a relatively homogeneous pore system. Therefore, the way fluids flow in sandstones may be modeled or controlled so that the hydrocarbon recovery is maximized. In contrast, carbonates often have a heterogeneous pore system. Typically, carbonates have two types of porosity systems: a micro (or matrix) porosity system with small grain-size pores mostly in inter-crystal and intra-crystal forms and a macro porosity system created by alteration of rock. In vuggy carbonates, the macro porosity system is dominated by vugs. Vugs are cavities, voids, or large pores in a rock. Vugs are typically caused by dissolution of the rock. Hereafter, a macro porosity system dominated by vugs will be referred to as a vug porosity system. When flow into a well occurs through two porosity systems, such as a matrix porosity system and a vug porosity system, the reservoir is known as a dual-permeability reservoir.

Historically, hydrocarbon recovery from dual-permeability reservoirs has been low because of lack of understanding of their complex nature. In vuggy carbonates, for example, well-connected vugs which result in very high permeability may concentrate in particular zones and areas of the reservoir. During production, it is common to inject water into the reservoir to sweep the hydrocarbons in various zones of the reservoir. The injected water may all flow into the super-permeability zones, also commonly known as "thief" zones. As a result, only the hydrocarbons in these thin super-permeability zones are swept and produced while the majority of hydrocarbons in the lower permeable zone are left un-swept. This is why hydrocarbon recovery from carbonates is generally much lower than from sandstones. Therefore, it is critical to accurately identify where the high-permeability zones and low-permeability zones are located before any production programs.

From the foregoing, there is desired a method of quantifying permeability of a vuggy reservoir.

SUMMARY OF INVENTION

In one aspect, the invention relates to a method for quantifying permeability of a vuggy reservoir which comprises determining a permeability modeled with matrix porosity ($K_0$) of the reservoir, determining a vug porosity ($\Phi_{vug}$) of the reservoir, and quantifying permeability (K) of the reservoir as follows:

$$K=aK_0 \cdot b^{c\Phi_{vug}},$$

where a, b, and c are constants.

In another aspect, the invention relates to a method for quantifying permeability of a vuggy reservoir which comprises identifying a plurality of vuggy and non-vuggy zones in the reservoir, obtaining a permeability modeled with matrix porosity for each of the vuggy and non-vuggy zones, determining a vug porosity for each vuggy zone, and, for each vuggy zone, boosting the permeability modeled with matrix porosity by a factor proportional to an exponential of the vug porosity for the vuggy zone.

In one aspect, the invention relates to a method for quantifying permeability of a dual-permeability reservoir which comprises determining a permeability modeled with matrix porosity ($K_0$) of the reservoir, obtaining a log of the reservoir comprising relative changes in resistively around a borehole penetrating the reservoir, transforming the log into a porosity map of the reservoir, estimating a vug porosity ($\Phi_{vug}$) of the reservoir from the porosity map, and quantifying permeability (K) of the reservoir as follows:

$$K=aK_0 \cdot b^{c\Phi_{vug}},$$

where a, b, and c are constants.

In another aspect, the invention relates to a method for quantifying permeability of a dual-permeability reservoir which comprises determining a permeability modeled with matrix porosity ($K_0$) of the reservoir, obtaining at least one description of a total porosity of the reservoir, estimating a vug porosity ($\Phi_{vug}$) of the reservoir from the description, and quantifying permeability (K) of the reservoir as follows:

$$K=aK_0 \cdot b^{c\Phi_{vug}},$$

where a, b, and c are constants.

Other features and advantages of the invention will be apparent from the following description and the appended claims.

BRIEF DESCRIPTION OF DRAWINGS

The invention is illustrated by way of example, and not by way of limitation, in the figures accompanying the drawings, and in which like reference numerals refer to similar elements, and in which.

DETAILED DESCRIPTION

The invention will now be described in detail with reference to a few preferred embodiments, as illustrated in the accompanying drawings. In the following description, numerous specific details are set forth in order to provide a thorough understanding of the invention. It will be apparent, however, to one skilled in the art, that the invention may be practiced without some or all of these specific details. In other instances, well-known process steps and/or features have not been described in detail in order to not unnecessarily obscure the invention. The features and advantages of the invention may be better understood with reference to the drawings and discussions that follow.

While not wishing to be bound by theory herein, the inventors believe herein that in vuggy sections of a reservoir, vug porosity has an exponential relation to permeability. The term "vug porosity" refers to the volume of the vugs expressed as a percent of the total rock mass. In a selected vuggy section of a reservoir, the vug porosity may be smaller than the matrix porosity, but the permeability component due to the vug porosity can still be higher than the permeability component due to the matrix porosity. This is because fluid can flow more easily in a cavity (or large pore) than in many small pores. The more connected the vugs are in a vuggy section, the higher the permeability can be in that vuggy section. Because of the exponential nature of vug porosity with respect to permeability, it can be seen that failure to properly account for the effect of vugs on permeability can lead to flooding of the high-permeability vuggy zones and a large amount of bypassed hydrocarbons.

In one embodiment, permeability of a vuggy reservoir has the following general expression: where K is permeability of the reservoir, $K_0$ is permeability of the reservoir modeled with matrix porosity or zero vug porosity, $\Phi_{vug}$ is vug porosity, and a, b and c are constants. It should be noted that the terms in equation (1) are distributions or curves. It should be noted that the term "zero vug porosity" does not preclude the presence of vugs. The term "zero vug porosity" generally means that the vug porosity is negligibly small in comparison to the matrix porosity. The term $K_0$ can be obtained by any of the conventional methods for obtaining permeability of a reservoir. The effect of the term $b^{c\Phi_{vug}}$ is to boost permeability of the vuggy zones to more accurately match actual permeability behavior of the reservoir in those zones.

Figure 1:
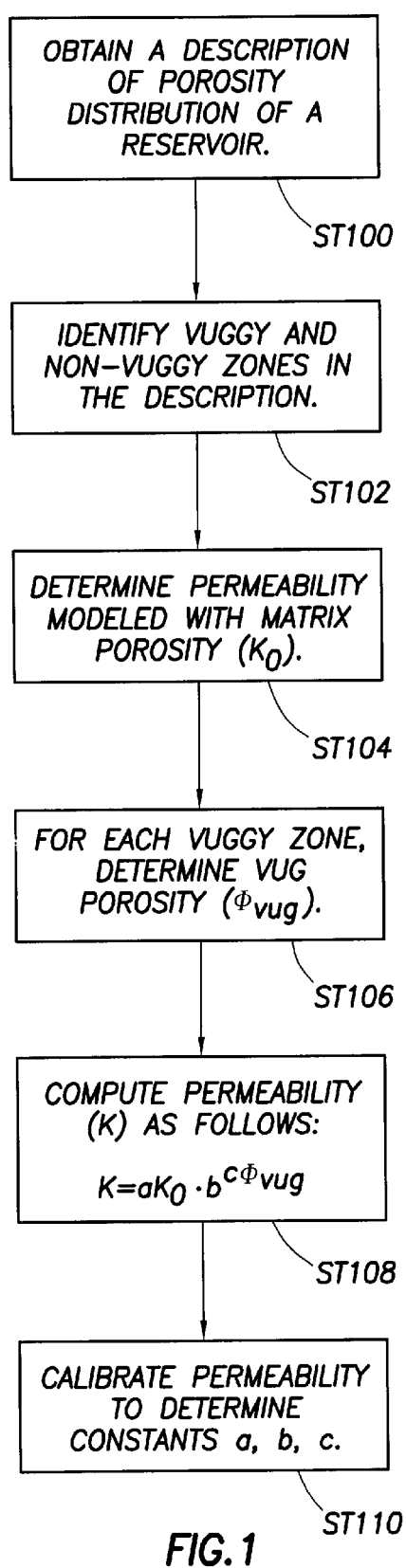
FIG. 1 is a flowchart illustrating a process for quantifying permeability of a vuggy carbonate reservoir according to one embodiment of the invention.

FIG. 1 is an overview of a process for quantifying permeability of a vuggy reservoir in accordance with one embodiment of the invention. The process starts, as shown at ST100, by receiving as input a description of the porosity distribution of the reservoir. Next, several vuggy and non-vuggy zones are identified in the description ST102). For all the zones, permeability modeled with matrix porosity or zero vug porosity, $K_0$, is determined (ST104). For each vuggy zone, the vug porosity, $\Phi_{vug}$, is determined (ST106). Then, the permeability modeled with matrix porosity, $K_0$, and the vug porosity, $\Phi_{vug}$, are used to quantify the permeability, K, of the reservoir, as stated in equation (1) above (ST108). Permeability is initially quantified with preset constants a, b, and c. The last step in the process is then to calibrate permeability to determine the actual values of the constants a, b, and c (ST110).

Figure 2:
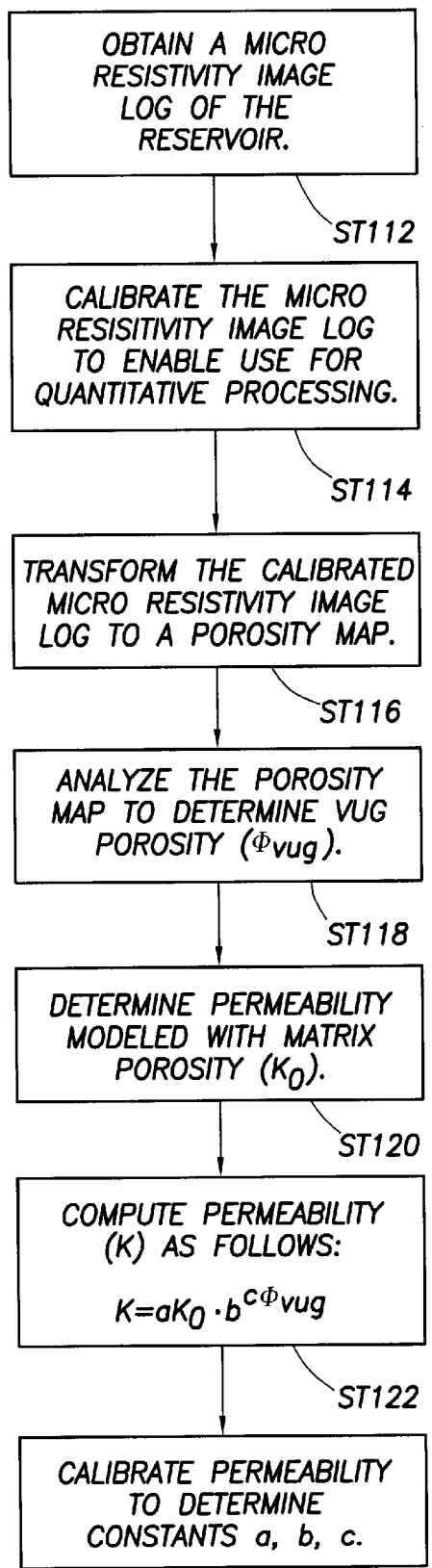
FIG. 2 is a more detailed view of the process described in FIG. 1 according to one embodiment of the invention.

FIG. 2 is a more detailed view of the process illustrated in FIG. 1 according to one embodiment of the invention. In the illustrated embodiment, the process starts by taking a micro-resistivity image log as input (ST112). The micro-resistivity image log is a series of curves (or data) representing relative changes of resistivity around a borehole penetrating the reservoir. The micro-resistivity image log has the resolution necessary to view the texture of the formation surrounding the borehole, so that vugs can be identified. Through a transformation process, which will be described later, a porosity map of the reservoir can be generated from the micro-resistivity image log. Ultimately, the porosity map will be used to determine vug porosity. In general, various types of logs, i.e., other than a micro-resistivity image log, can be used, to estimate vug porosity. A process that estimates vug porosity from conventional logs will be described later.

There are tools on the market that can be used to generate a micro-resistivity image log, such as one sold under the trade name Fullbore Formation MicroImager (FMI is a mark of Schlumberger Technology Corporation). A typical micro-resistivity imager includes a set of pads, where each pad is provided with a dense array of electrodes. During logging, the tool is positioned in the borehole and the pads are applied against respective sectors of the borehole wall as the tool is moved up the borehole. Each electrode emits an electrical current that is representative of relative micro changes in the resistivity of the formation facing that electrode. The set of measurements from each electrode are then combined to produce electrical images of the borehole wall, which are referred to herein as the micro-resistivity image log.

Figure 3:
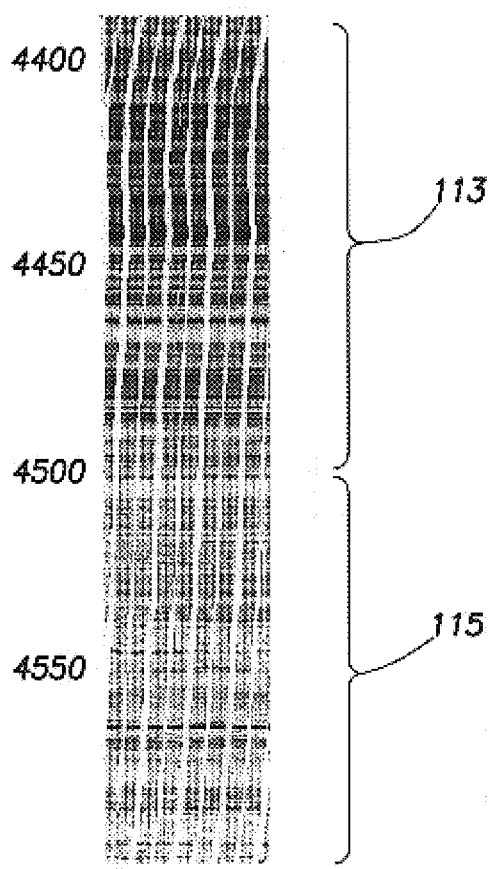
FIG. 3 is an example of a micro-resistivity image log.

As previously mentioned, the micro-resistivity image log is a series of curves (or data) representing relative changes of resistivity around the borehole. The micro-resistivity image log can be used to visualize the texture of the formation around the borehole. FIG. 3 shows an example of a micro-resistivity image log. The vertical axis of the log corresponds to borehole depth. The upper section 113 of the image log, which appears denser, is characterized by relatively homogeneous porosity, whereas the lower section 115 shows a considerable spread in porosity values due to the presence of vugs. Again, this does not mean that there are no vugs in the upper section 113. Rather, if vugs are present in the upper section 113, they have negligible effect on the porosity distribution in that section.

Returning to FIG. 2, after receiving the micro-resistivity image log, the log is calibrated (ST114). One reason for calibrating the micro-resistivity image log is that the micro-resistivity image log contains relative micro-resistivity changes around the borehole instead of true (or absolute) formation resistivity. (It should be noted that the conventional formation resistivity log, which contains true formation resistivity, does not have the fine resolution neither along the borehole nor around the bore to allow the texture of the formation around the borehole to be visualized.) To use the micro-resistivity image log for quantitative processing such as in this invention, it needs to be calibrated to a true formation resistivity log of similar investigation depth, e.g., a flushed zone around the borehole.

The next step in the process involves converting the calibrated micro-resistivity image log to a porosity map (ST116). As an example, the classic Archie saturation equation in the flushed zone can be used to transform the calibrated micro-resistivity image log into a porosity map. The classic Archie saturation equation has the general form:

$$S_{xO}^n = \frac{aR_{mf}}{\Phi^m R_{xO}} \quad (2)$$

where $S_{xO}$ is water saturation in flushed zone, $R_{mf}$ is mud filtrate resistivity, $R_{xO}$ is flushed zone resistivity, and $\Phi$ is porosity. By setting a=1.0 and m=n=2, which are typical values for carbonates, $\Phi$=PXND, and $R_{xO}$=LLS, equation (2) can be rewritten as:

$$S_{xO}^2 = \frac{R_{mf}}{PXND^2 \times LLS} \quad (3)$$

PXND is neutron-density, crossplot porosity or any porosity data that matches with core data. Neutron-density, crossplot porosity is obtained by plotting density and neutron porosity logs against each other. LLS (lateral log shallow) is formation resistivity near the borehole, e.g., in a flushed zone around the borehole.

The water saturation, $S_{xO}$, may also be computed using the calibrated micro-resistivity image log data as follows:

$$S_{xO}^2 = \frac{R_{mf}}{\Phi_{mri}^2 \times R_{mri}} \quad (4)$$

where $\Phi_{mri}$ is the total porosity to be computed from the calibrated micro-resistivity image log, $R_{mri}$ is the resistivity from the calibrated micro-resistivity image log, and $R_{mf}$ is mud filtrate resistivity. Equating equations (3) and (4) and solving for $\Phi_{mri}$, the following expression is obtained:

$$\Phi_{mri} = PXND \sqrt{\frac{LLS}{R_{mri}}} \quad (5)$$

Using equation (5) above, the calibrated micro-resistivity image log can be transformed into a porosity map around the borehole.

Figure 4:
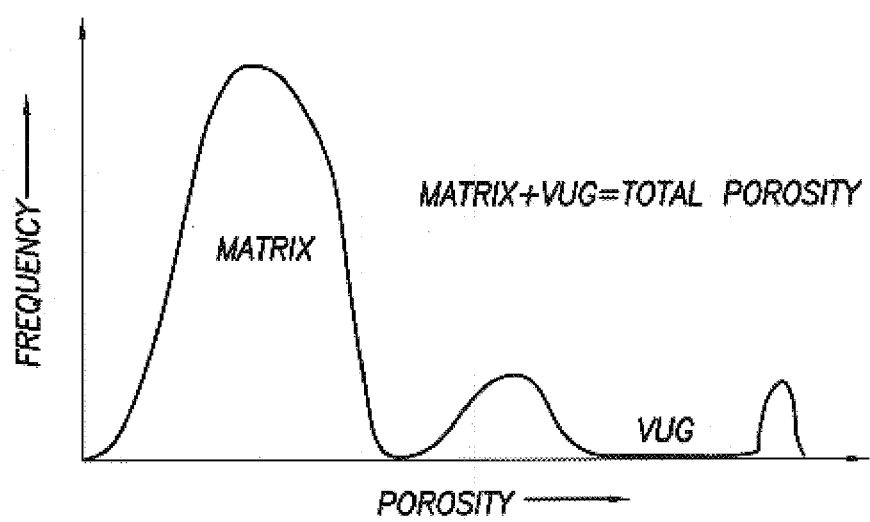
FIG. 4 is a typical histogram of porosity of a dual-permeability reservoir.

The next step in the process involves analyzing the porosity map to identify the matrix porosity distribution and the vug porosity distribution (ST118). A method of identifying the primary and secondary porosity distributions in a porosity map is described in B. M. Newberry and L. M. Grace, "Analysis of Carbonate Dual Porosity Systems from Borehole Electrical Images,"SPE 35158, 1996. Basically, the porosity map can be divided into multiple regions. For each region, the porosity distribution is statistically examined to locate the porosity value that separates the matrix porosity from the vug porosity. For example, a histogram can be generated for each region. FIG. 4 shows a typical histogram of porosity. For regions that contain only evenly distributed matrix porosity, only one peak will be seen on the histogram. For regions that contain vugs, multiple peaks are seen on the histogram. From the histograms, the porosity value that marks the separation of the porosity data into matrix and vug porosity systems can then be statistically located.

Returning to FIG. 2, the next step in the process is to obtain permeability of the reservoir modeled with matrix porosity or zero vug porosity, i.e., $K_0$ in equation (1), (ST120). As previously noted, any suitable (or conventional) method for calculating permeability can be used to obtain $K_0$. For example, $K_0$ for all zones can be computed using Coates/Timur equation. Coates/Timur equation is well known in the art. For example, conductivity can be used to determine $K_0$ because $K_0$ generally has a linear relationship with conductivity. The constant of proportionality between $K_0$ and conductivity can be factored into the constant a in equation (1). The conductivity values can be obtained from the calibrated micro-resistivity image log (obtained in ST114), where conductivity is the inverse of resistivity.

With the vug porosity, $\Phi_{vug}$, obtained from ST118 and the permeability modeled with matrix porosity, $K_0$, obtained from ST120, the permeability of the reservoir can now be quantified using equation (1) (ST122). The last step involves calibrating permeability to determine the constants a, b, and c in equation (2) (ST114). When vug porosity, $\Phi_{vug}$, is zero, equation (1) reduces to $K=aK_0 \cdot K_0$ is already known, i.e., determined at step ST120. The term $aK_0$ can be equated to core permeability. The core permeability is obtained by taking actual samples of the formation at various depths along the borehole and measuring the permeability of the samples in a laboratory. With $aK_0$ and $K_0$ known, the constant a can be easily determined. Again, the constant a is more like a distribution instead of a single value. Once $aK_0$ is known, the constants b and c are determined by again matching K with core permeability of vuggy zones at selected vug porosities.

As previously mentioned, the invention is not limited to use of a micro-resistivity image log as input for computing vug porosity. In the embodiment shown in FIG. 5, a combination of conventional logs is used for computing vug porosity about a borehole.

Figure 5:
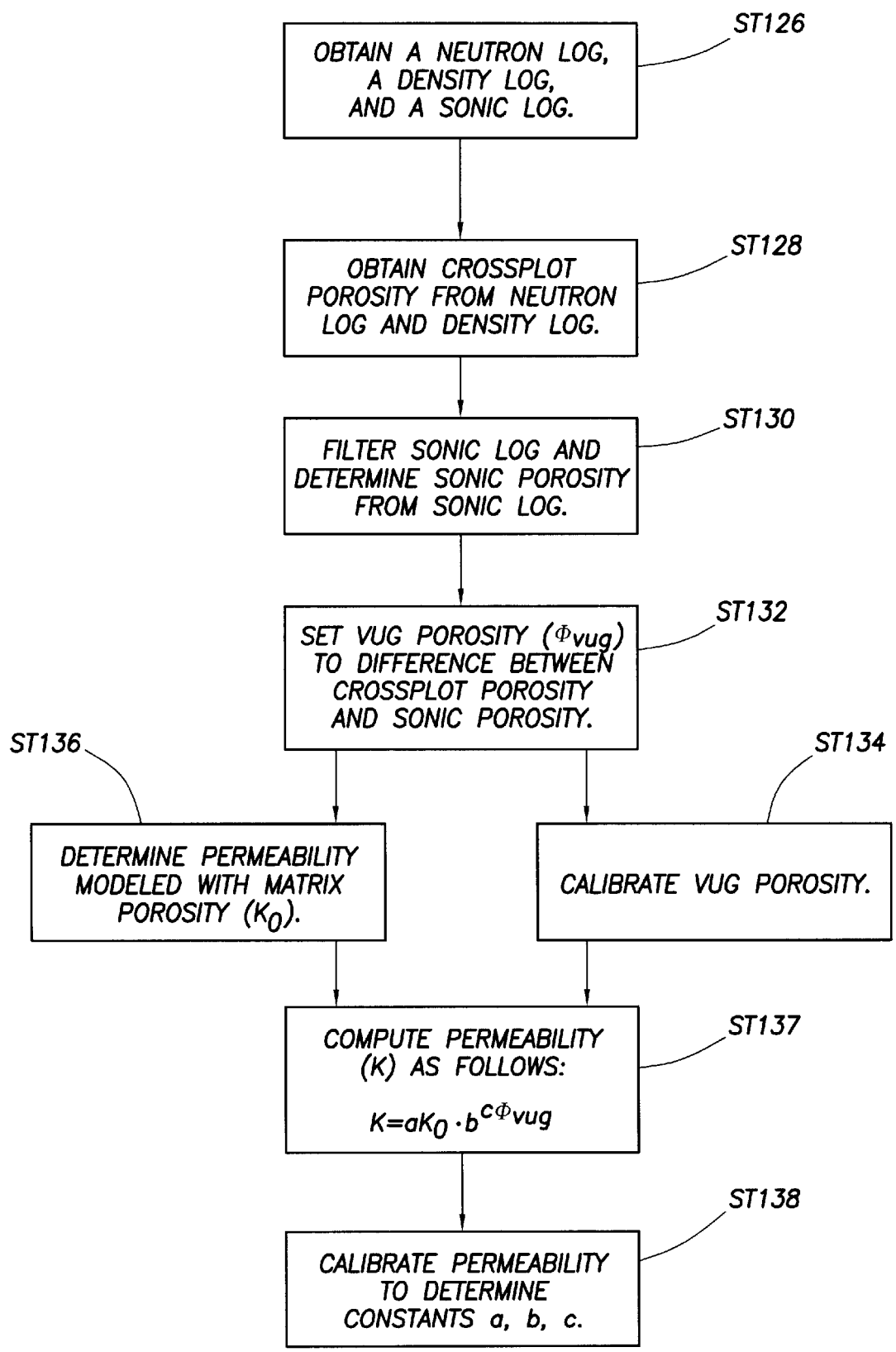
FIG. 5 is a more detailed view of the process described in FIG. 1 according to another embodiment of the invention.

FIG. 5 shows a process for quantifying permeability of a reservoir according to another embodiment of the invention. The process starts by receiving a neutron log, a density log, and a sonic log as input (ST126). Next, neutron-density, crossplot porosity is obtained by plotting the neutron log and density log against each other (ST128). Generation of crossplot porosity from neutron and density logs is standard procedure in the art. It should be noted that the crossplot porosity may be given as an input instead of the neutron and density logs, eliminating the need for step ST128. The sonic log is filtered to remove noise, and sonic porosity is determined from the sonic log (ST130).

The crossplot porosity and sonic porosity each contain a different description of the total porosity distribution of the reservoir. In the sonic porosity, the compression sonic waves used in sonic logging generally bypass isolated vugs in carbonates. From observation, the missing portion of the total porosity from the sonic log is proportional to the total vug porosity, i.e., vug porosity due to isolated and connected vugs. Thus, the difference between the crossplot porosity and the sonic porosity generally gives a good estimate of vug porosity. In accordance with one embodiment of the invention, vug porosity is then estimated as the difference between the crossplot porosity and the sonic porosity (ST132). Next, the vug porosity obtained in ST132 is calibrated such that it is zero in the non-vuggy zones (ST134).

The next step is to determine the permeability of the reservoir modeled with matrix porosity or zero vug porosity, i.e., $K_0$ in equation (1), (ST136). As previously mentioned, any suitable (or conventional) method for calculating permeability of a reservoir can be used to obtain $K_0$, e.g., Coates/Timur equation can be used to determine the permeability. For example, conductivity can be used to determine $K_0$ because permeability generally has a linear relationship with conductivity at zero vug porosity. Using the vug porosity obtained in ST132 and the permeability modeled with matrix porosity obtained in ST136, the permeability of the reservoir can be quantified, as stated in equation (1). The last step in the process would then be to determine the constants a, b, and c (ST138), as previously described.

The invention provides one or more advantages. The invention provides a practical and accurate method for quantifying permeability of a vuggy reservoir. The invention works by boosting the permeability of the vuggy zones such that the permeability of the vuggy zones matches the core permeability measurements. It should be noted that the core permeability measurements, while accurate, are made at few selected points along the length of the borehole. What the invention offers is a method for obtaining a continuous distribution of permeability along a length of a borehole at almost real time, which offers tremendous flexibility when it comes to production planning/optimization.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A method for quantifying permeability of a vuggy reservoir, comprising:

determining a permeability modeled with matrix porosity ($K_0$) of the reservoir;

determining a vug porosity ($\Phi_{vug}$) of the reservoir; and quantifying permeability (K) of the reservoir as follows:

$$K = aK_0 \cdot b^{c\Phi_{vug}}$$

where a, b, and c are constants.

2. The method of claim 1, wherein determining the vug porosity of the reservoir comprises obtaining a description of a total porosity of the reservoir.

3. The method of claim 2, wherein obtaining the description of the total porosity of the reservoir comprises obtaining a log containing relative changes in resistivity around a borehole penetrating the reservoir.

4. The method of claim 3, wherein determining the vug porosity of the reservoir further comprises transforming the log into the total porosity.

5. The method of claim 4, wherein determining the vug porosity of the reservoir further comprises statistically examining the total porosity to locate a porosity value separating the vug porosity from the matrix porosity of the reservoir.

6. The method of claim 1, wherein determining the vug porosity of the reservoir comprises obtaining two independent descriptions of a total porosity of the reservoir.

7. The method of claim 6, wherein determining the vug porosity of the reservoir further comprises estimating the vug porosity from the two independent descriptions of the total porosity of the reservoir.

8. The method of claim 1, further comprising determining the constant a by setting the permeability (K) to a core permeability at a selected number of depths in the reservoir where the vug porosity has a negligible value in comparison to the matrix porosity of the reservoir.

9. The method of claim 8, further comprising determining the constants b and c by setting the permeability (K) to a core permeability at a selected number of depths in the reservoir where the vug porosity is greater than zero.

10. A method for quantifying permeability of a vuggy reservoir, comprising:

identifying a plurality of vuggy and non-vuggy zones in the reservoir;

obtaining a permeability modeled with matrix porosity for each of the vuggy and non-vuggy zones;

determining a vug porosity for each vuggy zone; and for each vuggy zone, boosting the permeability modeled with matrix porosity by a factor proportional to an exponential or the vug porosity for the vuggy zone.

11. The method of claim 10, wherein the factor is $b^{c\Phi_{vug}}$, where b and c are constants and $\Phi_{vug}$ represents the vug porosity.

12. The method of claim 10, wherein determining the vug porosity for each vuggy zone comprises obtaining a description of a total porosity of the reservoir.

13. The method of claim 12, wherein obtaining a description of the total porosity of the reservoir comprises obtaining a log containing relative changes in resistivity around a borehole penetrating the reservoir.

14. The method of claim 13, wherein determining the vug porosity for each vuggy zone further comprises transforming the log into the total porosity and statistically examining the total porosity to locate a porosity value separating the vug porosity from the matrix porosity in the vuggy zone.

15. The method of claim 10, wherein determining the vug porosity for each vuggy zone comprises obtaining two independent descriptions of a total porosity of the reservoir.

16. The method of claim 15, wherein determining the vug porosity for each vuggy zone further comprises estimating the vug porosity from the two independent descriptions of the total porosity of the reservoir.

17. A method for quantifying permeability of a dual-permeability reservoir, comprising:

determining a permeability modeled with matrix porosity ($K_0$) of the reservoir;

obtaining a log of the reservoir comprising relative changes in resistivity around a borehole penetrating the reservoir;

transforming the log into a porosity map of the reservoir;

estimating a vug porosity ($\Phi_{vug}$) of the reservoir from the porosity map; and quantifying permeability (K) of the reservoir as follows:

$$K = aK_0 \cdot b^{c\Phi_{vug}}$$

where a, b, and c are constants.

18. A method for quantifying permeability of a dual-permeability reservoir, comprising:

determining a permeability modeled with matrix porosity ($K_0$) of the reservoir;

obtaining at least one description of a total porosity of the reservoir;

estimating a vug porosity ($\Phi_{vug}$) of the reservoir from the description; and quantifying permeability (K) of the reservoir as follows:

$$K = aK_0 \cdot b^{c\Phi_{vug}}$$

where a, b, and c are constants.

19. The method of claim 18, wherein the description comprises a log containing relative changes in resistivity around a borehole penetrating the reservoir.

20. The method of claim 19, wherein estimating the vug porosity comprises transforming the log into a porosity map and statistically examining the porosity map to locate a porosity value separating the vug porosity from the matrix porosity of the reservoir.

* * * * *